US007347837B2

(12) United States Patent
Azzolini

(10) Patent No.: US 7,347,837 B2
(45) Date of Patent: Mar. 25, 2008

(54) INFUSION PUMP FOR SYRINGES

(76) Inventor: Graziano Azzolini, Via S. Anna, 3/R, 41032 Cavezzo (IT)

( * ) Notice: Subject to any disclaimer, the term of this patent is extended or adjusted under 35 U.S.C. 154(b) by 0 days.

(21) Appl. No.: 11/050,836

(22) Filed: Feb. 7, 2005

(65) Prior Publication Data

US 2005/0177109 A1    Aug. 11, 2005

(30) Foreign Application Priority Data

Feb. 6, 2004    (IT)    .................... MO2004A0028

(51) Int. Cl.
*A61M 37/00*    (2006.01)
(52) U.S. Cl. .................. 604/154; 604/151; 366/163.2; 366/110; 366/210; 366/239
(58) Field of Classification Search .................. 604/67, 604/118, 154, 155, 151; 366/163.2, 110, 366/210, 239, 160.4, 267, 268, 208, 209; 222/137
See application file for complete search history.

(56) References Cited

U.S. PATENT DOCUMENTS

| 3,631,847 | A | | 1/1972 | Hobbs |
| 4,585,009 | A | * | 4/1986 | Barker et al. ................ 600/432 |
| 4,838,857 | A | | 6/1989 | Strowe et al. |
| 5,814,015 | A | * | 9/1998 | Gargano et al. .............. 604/67 |
| 6,221,045 | B1 | * | 4/2001 | Duchon et al. .............. 604/151 |
| 6,575,930 | B1 | * | 6/2003 | Trombley et al. ............. 604/82 |
| 6,726,657 | B1 | * | 4/2004 | Dedig et al. ................. 604/152 |
| 6,743,205 | B2 | * | 6/2004 | Nolan et al. ................. 604/154 |
| 6,821,013 | B2 | * | 11/2004 | Reilly et al. .............. 366/162.3 |
| 2002/0025267 | A1 | * | 2/2002 | Lieber et al. ................ 417/572 |
| 2003/0117888 | A1 | | 6/2003 | Reilly et al. |

FOREIGN PATENT DOCUMENTS

| WO | WO 98/00187 A | 1/1998 |
| WO | WO 00/53242 A | 9/2000 |
| WO | WO 01/08727 A | 2/2001 |
| WO | WO 01/97901 A | 12/2001 |

* cited by examiner

*Primary Examiner*—Kevin C. Sirmons
*Assistant Examiner*—Laura C. Schell
(74) *Attorney, Agent, or Firm*—Andrew Wilford

(57) ABSTRACT

An infusion pump has a base and a holder for a syringe extending along a longitudinal axis and having an axially shiftable plunger. The holder is pivotal on the base about a first axis substantially perpendicular to the longitudinal axis of the syringe. A first actuator connected between the base and the holder can oscillate the holder about the first axis relative to the base. A pusher is displaceable linearly on the base transversely of the first axis by a second actuator that can press this pusher against the plunger and thereby slide the plunger of the syringe and empty the syringe's contents. A controller is connected to the first and second actuators for moving the pusher out of engagement with the plunger during oscillation of the syringe and for operating the second actuator only when the first actuator is not oscillating the syringe to express the contents of the syringe.

28 Claims, 5 Drawing Sheets

INFUSION PUMP FOR SYRINGES

FIELD OF THE INVENTION

Infusion pumps for syringes, which are used in the therapeutic field for the controlled and automated infusion of drugs, are known.

BACKGROUND OF THE INVENTION

Known pumps are substantially constituted by a supporting frame with which means for locking the cylindrical body of a syringe and means of the linear automated type for actuating the sliding of the plunger of the syringe are associated.

An electronic circuit controls and actuates the actuation means in order to dispense the drug contained in the syringe according to an infusion program (time, flow-rate, speed etc.) that can be set from the outside by a health operator by means of a keypad and a display.

These known types of pump are not free from drawbacks, including the fact that if the fluid to be infused is constituted by a plurality of components they do not allow them to mix adequately as required.

Currently, mixing is performed manually by health operators, who shake the syringe into which the components of the fluid have been introduced, with consequent disadvantageous labor costs and long execution times and producing a homogenization that is imperfect and inconstant since it depends on the experience and dexterity of the operators.

Another drawback of known pumps is that they practically cannot be used to infuse fluids that contain microbubbles of air or gas, such as for example the contrast media used in imaging diagnostic methods, such as in particular echocontrast imaging.

The expression "echocontrast imaging" designates a sonogram that uses contrast media and utilizes the reflection of ultrasound by microbubbles entrained together with the contrast medium.

The infusion of these fluids must in fact follow immediately their mixing in order to prevent the microbubbles from distributing unevenly inside them, and therefore to prevent the fractions of fluid that are infused in succession from containing too many or too few microbubbles, compromising the quality of the sonograms.

For this reason, the operator assigned to mixing them manually also then injects them manually immediately thereafter into the line for infusion to a patient; the time required to prepare a known type of pump would in fact eliminate the effects of mixing.

Currently, therefore, the mixing and infusion of these fluids that contain microbubbles of air or gas, as well as the immediate successive infusion of a physiological solution, are entirely manual, and this accordingly entails a further disadvantageous increase in labor costs and in execution times as well as inevitable and unpredictable inaccuracies and errors in execution due to the experience and dexterity of the operators.

Moreover, it should be noted that the contrast media of this type have high intrinsic costs, and therefore their incorrect mixing and/or their incorrect infusion, such as to compromise for example the quality of the resulting sonogram and prevent correct diagnosis, entail a waste of material that is disadvantageously onerous.

OBJECTS OF THE INVENTION

The aim of the present invention is to eliminate the above-mentioned drawbacks of known pumps, by providing an infusion pump for syringes that allows the components of a fluid to be mixed and then infused uniformly and constantly, to reduce labor use and costs, to reduce the time required, and to limit errors in mixing.

Another object of the present invention is to provide a pump that can be used easily to mix and infuse fluids that contain air or gas microbubbles uniformly, precisely and constantly and that reduces waste of material.

Another object of the present invention is to provide an infusion pump that can be used particularly to infuse contrast media and optionally physiological solutions for echocontrast imaging.

Within this aim, another object of the present invention is to provide an infusion pump that is simple, relatively easy to provide in practice, safe in use, effective in operation, and that has a relatively low cost.

SUMMARY OF THE INVENTION

This aim and these and other objects that will become better apparent hereinafter are achieved by the present infusion pump for syringes, characterized in that it comprises a supporting structure, means for supporting a syringe that can be rigidly mounted on the syringe and can be mounted on the supporting structure so that they can rotate alternately about an axis that is substantially perpendicular to the longitudinal axis of the syringe, first means for actuating the alternating rotation and second means for actuating the sliding of the plunger of the syringe, which cooperate functionally with the first actuation means.

BRIEF DESCRIPTION OF THE DRAWINGS

Further characteristics and advantages of the present invention will become better apparent from the following detailed description of a preferred but not exclusive embodiment of an infusion pump for syringes, illustrated by way of non-limiting example in the accompanying drawings, wherein.

DESCRIPTION OF THE PREFERRED EMBODIMENTS

Figure 1:
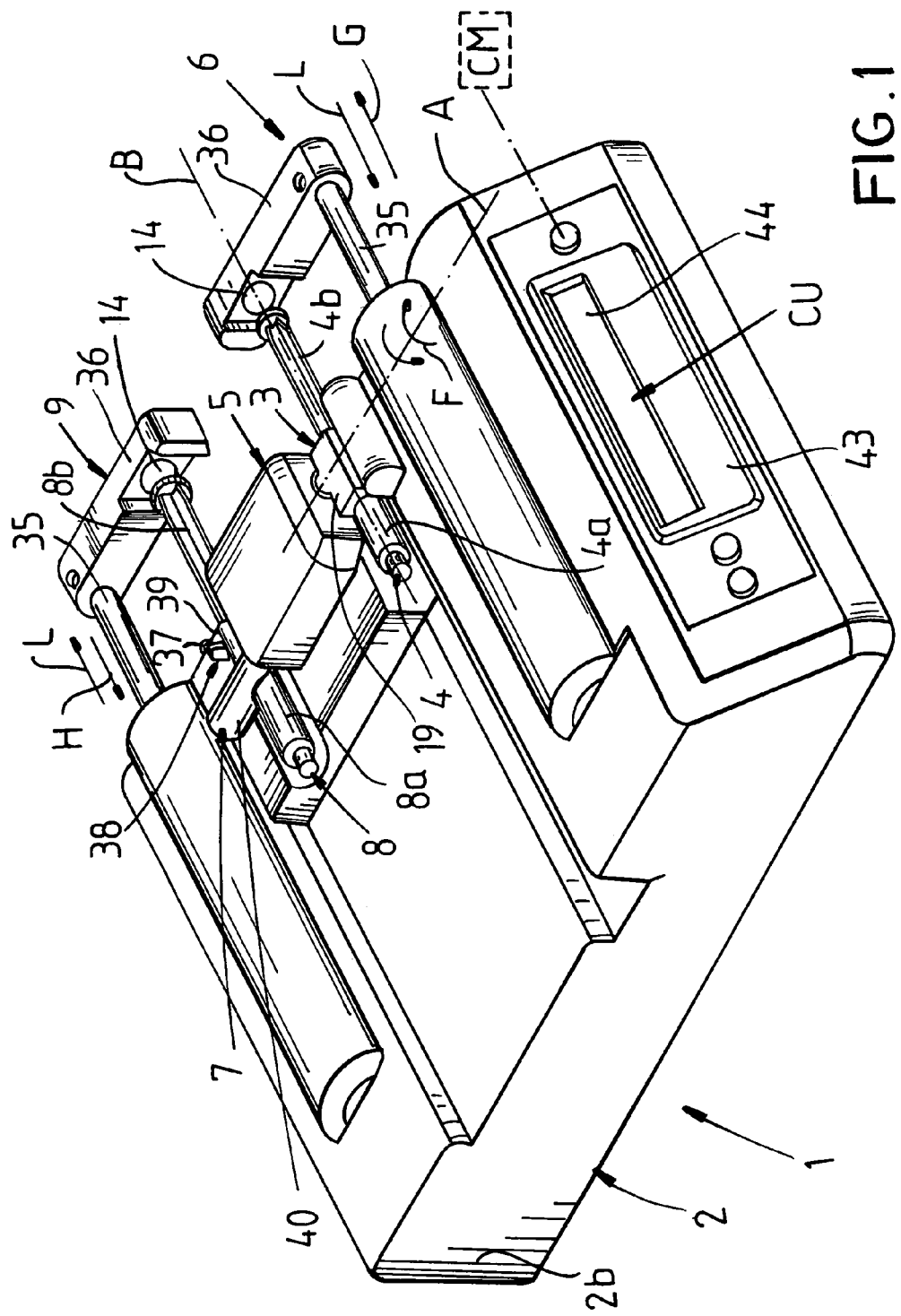
FIG. 1 is a schematic axonometric view of an infusion pump for syringes according to the invention.
Figure 2:
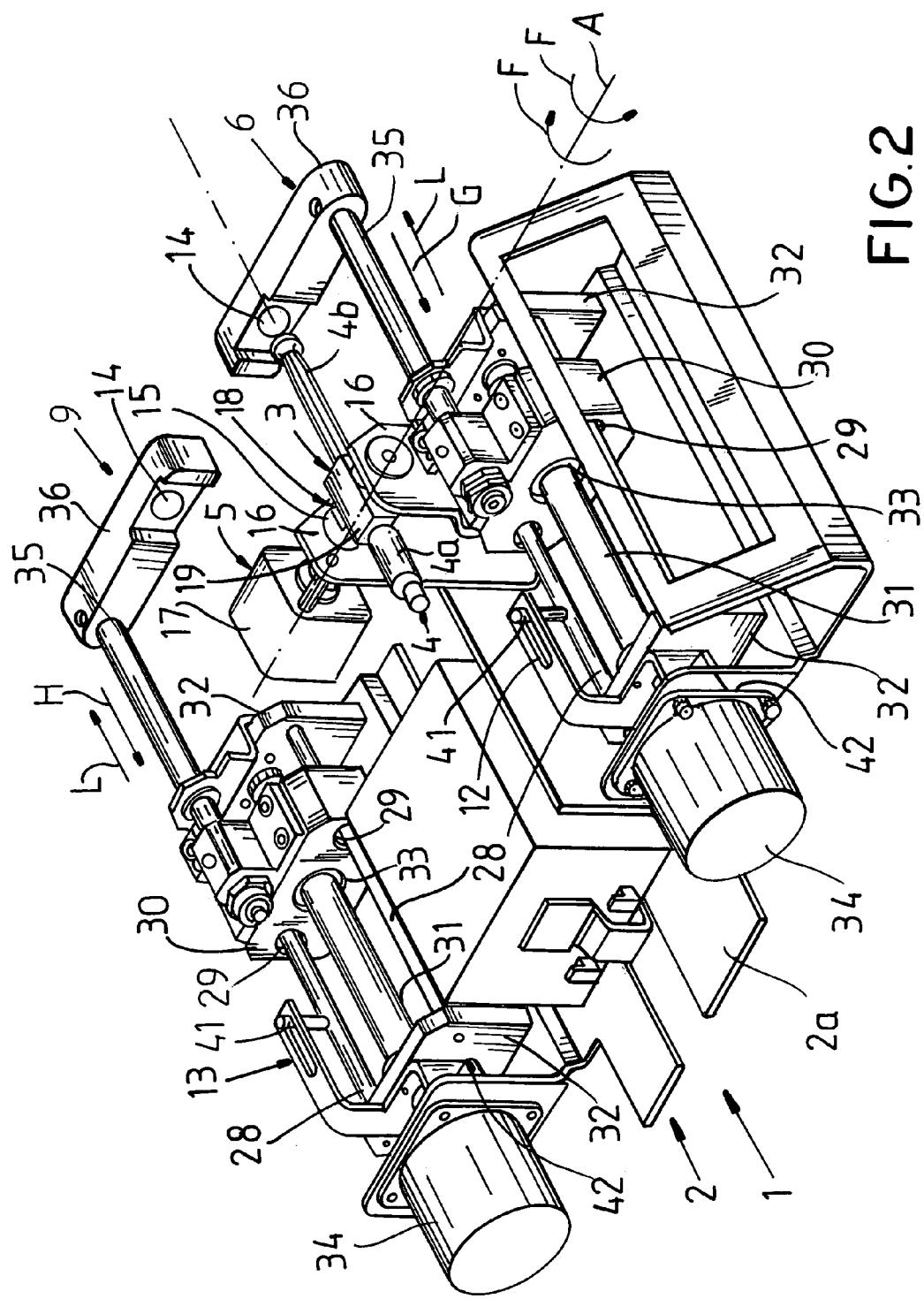
FIG. 2 is a schematic axonometric view of the pump of FIG. 1 without the covering and protective housing.

With reference to the figures, the reference numeral 1 generally designates an infusion pump for syringes.

The pump 1 comprises a supporting structure 2, which is divided into a base 2a and a housing 2b, means 3 for supporting a syringe 4 of the type constituted by a cylindrical body 4a inside which a plunger 4b slides, which can be rigidly mounted on the syringe 4 and can be detachably mounted on the supporting structure 2 so as to rotate alternately about a first axis A that is substantially perpendicular to a second longitudinal axis B of the syringe 4.

The syringe 4, which is rigidly coupled to the holder 3, is therefore alternately rotated about the axis A with a so-called oscillating or rocking motion.

Further, the pump 1 comprises first actuation means 5 of the automated type for actuating the alternating rotation of the holder 3 and therefore of the syringe 4 that is rigidly coupled thereto. The first actuation means 5 cooperates functionally with second actuation means 6 of the automated type for sliding of the plunger 4b.

Conveniently, the axis A lies on a substantially horizontal plane while the alternated rotation angle has a breadth of less than 2 $\pi$rad.

Further, the pump 1 comprises means 7 for locking an auxiliary syringe 8 of the type that is constituted by a cylindrical body 8a inside which a plunger 8b slides. This means 7 is mounted on the housing 2b, and third actuation means 9 of the automated type for actuating the sliding of the plunger 8b.

Figure 3:
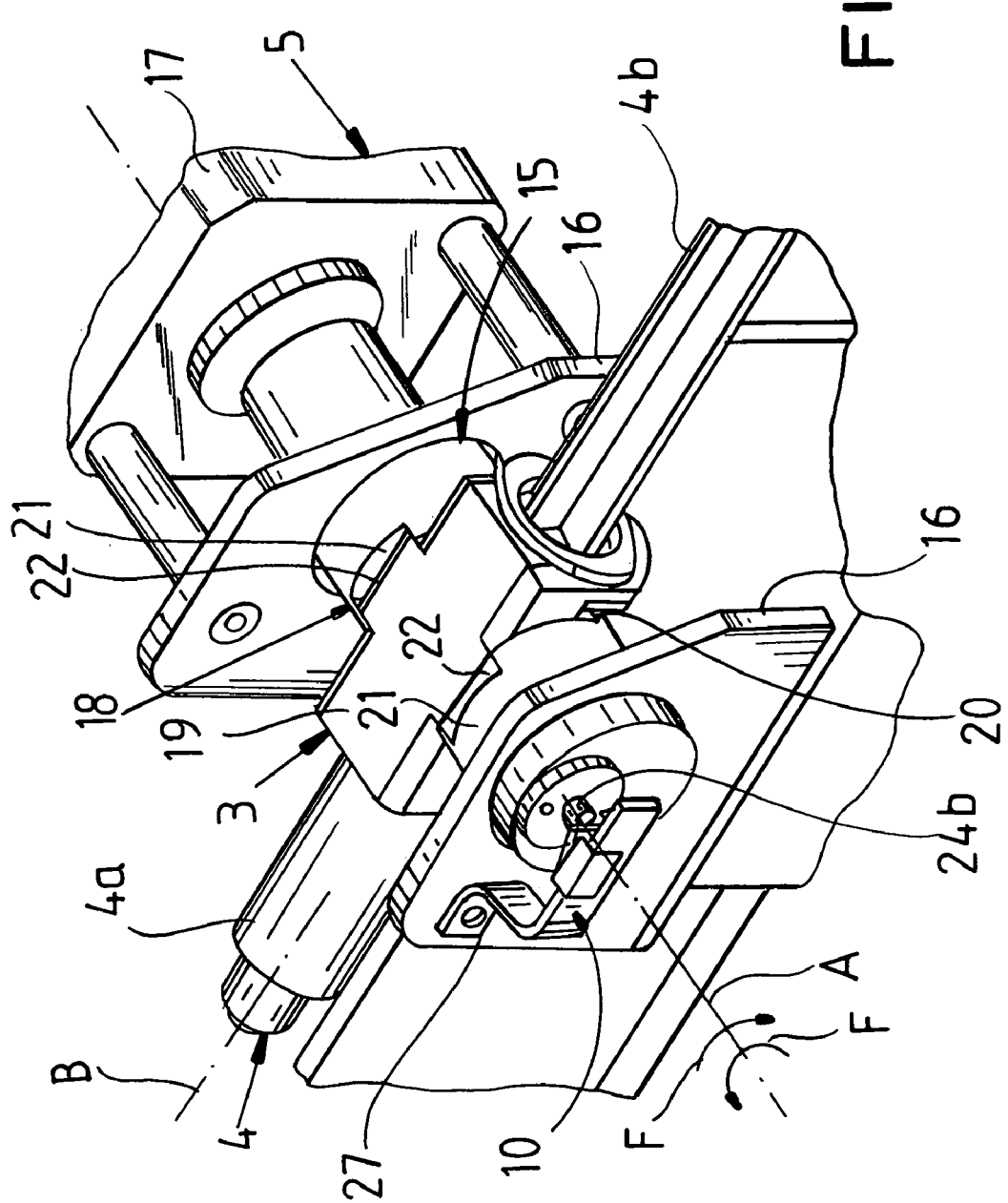
FIG. 3 is a schematic enlarged-scale axonometric view of a detail of the holder and of the first actuation means of the pump according to the invention.
Figure 4:
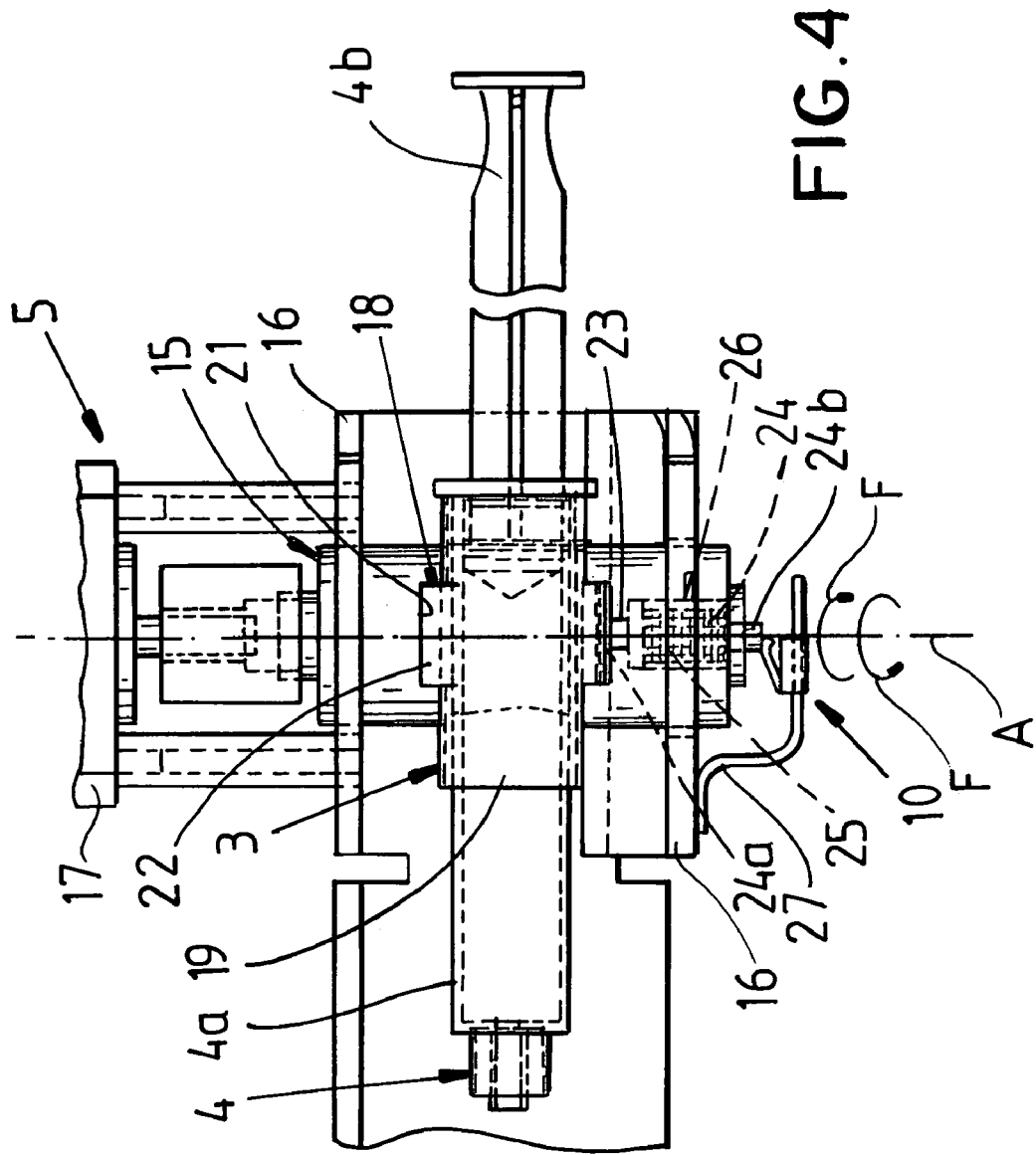
FIG. 4 is a schematic top plan view of the detail of FIG. 3.
Figure 6:
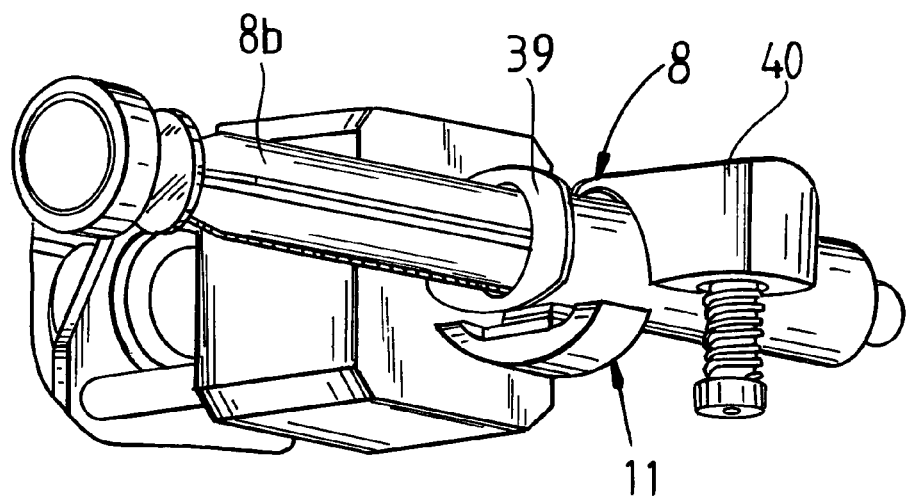
FIG. 6 is a schematic axonometric enlarged-scale view of a detail of the means for locking the auxiliary syringe of the pump according to the invention.

First sensing means 10 (FIGS. 3 and 4) and second sensing means 11 (FIG. 6), such as for example on/off switches, detect the presence of the syringe 4 and of the auxiliary syringe 8 respectively; first control means 12 and second control means 13 control the sliding of the respective plungers 4b and 8b; and means 14 for sensing the pressure applied to the plungers 4b and 8b are associated respectively with the second actuation means 6 and with the third actuation means 9.

The second actuation means 6 and the third actuation means 9 are of the linear type. The first actuation means 5, the second actuation means 6 and the third actuation means 9 can be, for example, of the mechanical, pneumatic, hydraulic (hydrodynamic), electric or electromechanical type.

The pump 1 is provided with ON/OFF control means shown schematically in FIG. 1 at CM for activating and deactivating its operation and that can be advantageously be operated a foot and are constituted for example by a pedal, a pushbutton or the like, for transmitting start and stop signals over a cable, wirelessly or via infrared.

An electronic control and monitoring unit CU, such as an electric controller, advantageously of the programmable type, is functionally connected to the first actuation means 5, with the second actuation means 6, and optionally with the first means 10 for sensing the syringe 4, with the first control means 12 for controlling the sliding of the plunger 4b, and with the means 14 for sensing the pressure applied to the plunger 4b.

If the auxiliary syringe 8 is also present, the electronic unit is also connected to the third actuation means 9, with the second means 11 for sensing the auxiliary syringe 8, with the second control means 13 for controlling the sliding of the plunger 8b, and with the means 14 for sensing the pressure applied to the plunger 8b.

The first actuation means 5, may for example comprise a shaft 15, which forms (extends along) the axis A and is supported, so that it can rotate in first supports 16 formed in the base 2a of the supporting structure 2, first motor means 17, which are coupled to the shaft 15, and means 18 for coupling the holder 3 to the shaft 15. Conveniently, the first motor means 17 are of the step motor type and comprise an inverter.

The holder 3 comprises a tubular element 19, inside which it is possible to insert the cylindrical body 4a of the syringe 4. Means for rigidly fixing the tubular element 19 to the cylindrical body 4a, for example of the interlocking, adhesive-bonding, or interference-coupling type, are provided. In a particular embodiment, not shown, the gripping means may comprise a longitudinal slot, which interrupts the continuity of the tubular element 19, the inside diameter of which, in the configuration in which it is disengaged from the cylindrical body 4a, is substantially smaller than the outside diameter of the cylindrical body 4a.

The coupling means 18 can be of the interlocking and/or contrast and/or friction type; they comprise for example a receptacle or seat 20 holding the holder 3, which is formed in the shaft 15 and is provided with cavities 21 in which it is possible to insert corresponding protrusions 22 formed in the holder 3.

Advantageously, the seat 20 has a profile that substantially duplicates the profile of the outer lateral surface of the holder 3.

Figure 5:
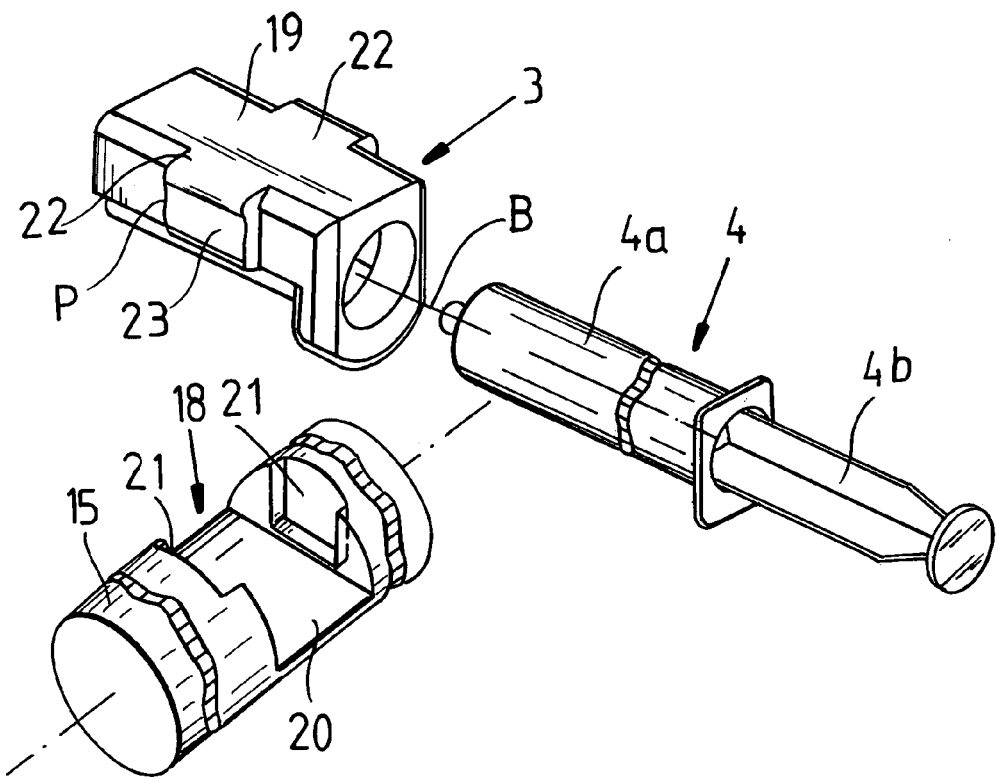
FIG. 5 is a schematic exploded view of the holder and of the first actuation means according to the invention.

Further, the holder 3 has a contoured portion 23 that has a contoured profile P (FIG. 5), which can mate with a complementarily contoured head 24a (FIG. 4) of a stem 24 that is inserted so that it can slide axially, with the interposition of elastic means 25, in a guide 26 that is formed at the free end of the shaft 15 at the seat 20. The head 24a protrudes into the seat 20 in order to mate with the portion 23 and push, by way of the reaction of the elastic means 25, against the holder 3 so as to fix them to the shaft 15.

The stem 24 has an end 24b positioned opposite the head 24a, which protrudes externally from the free end of the shaft 15, proximate to which the first sensing means 10 are arranged. The sensing means are supported by a plate 27, which is fixed to the corresponding first support 16.

Insertion of the holder 3 in the seat 20 produces the sliding of the stem 24 toward the outside of the shaft 15, so that the end 24b acts on the first sensing means 10, which being thus activated report the presence of the holder 3 and therefore of the syringe 4 rigidly coupled thereto.

Each one of the second actuation means 6 and of the third actuation means 9 comprises straight guiding means 28, along which a slider 30 is associated so that it can slide alternately by way of bushes 29, driven by a screw 31, which is substantially parallel to the straight guiding means 28 and is supported so that it can rotate by second supports 32 formed in the base 2a of the supporting structure 2 and is coupled to a female thread 33 formed in the slider 30, and second motor means 34, which are carry the screw 31.

The slider 30 rigidly supports the end of a bar 35. A pusher 36 is fixed to the opposite end of the bar and can contact the plunger 4b or 8b, respectively, of the syringe 4 and of the auxiliary syringe 8. Conveniently, the second motor means 34 are of the step motor type and comprise an inverter.

The pressure sensing means 14, constituted for example by a load cell, are fixed to the face of the pusher 36 that makes contact with the plunger 4b or 8b.

The means 7 for locking the auxiliary syringe 8 may be constituted for example by a receptacle, such as a slot 37 (FIG. 1) formed in a block 38 that is fixed to the housing 2b, inside which it is possible to insert wings 39 formed at the inlet end of the cylindrical body 8a, and a clamp 40 for locking the cylindrical body 8a.

The first control means 12 and the second control means 13 comprise respective proximity sensors 41, switches or the like, which can detect the position of the corresponding slider 30 and/or sensors 42 for detecting the rotation of the corresponding screw 31.

A keypad 43 (FIG. 1) and a display 44 anchored to the housing 2b allow to the operator select/set and monitor the operating program of the pump 1.

With particular but not exclusive reference to a setup wherein the pump 1, which comprises not only the means 3 for supporting the syringe 4 but also the means 7 for locking the auxiliary syringe 8, is used to perform sonograms with a contrast medium (echocontrast sonograms), the operation of the invention is as follows:

The echocontrast sonogram technique provides for the infusion in succession of a contrast medium that contains gas microbubbles and of a physiological solution, in quantities, with rates and with a time interval between the first infusion and the second infusion that can vary according to the type of diagnosis to be performed and according to the physical characteristics of the individual patient (weight, age, etc.)

The syringe 4, to which the holder 3 is already rigidly anchored, and which is filled with a preset quantity of contrast medium, and the auxiliary syringe 8, filled with a preset quantity of physiological solution, are purged manually, the term "purging" being understood to designate the action meant to eliminate any residues of air contained in the syringes.

Once the operating program has been selected by means of the keypad 43, the two syringes 4 and 8 are anchored to the pump 1. In particular, the holder 3 is rigidly coupled to the shaft 15, while the cylindrical body 8a of the syringe 8 is anchored to the housing 2b by way of the locking means 7.

The first sensing means 10 and the second sensing means 11 report the presence of the syringe 4 and of the auxiliary syringe 8, respectively, to the electronic control and monitoring unit CU.

The outlets of the two syringes 4 and 8 are connected to the inlets of a conventional infusion line of the Y-shaped type, the output of which is suitable to be connected to a tube for feeding to a patient.

By means of a command inputted at the keypad 43, the shaft 15 is actuated by the first motor means 17 so as to oscillate about the axis A through a preset angle, as shown by the arrows F. The microbubbles of the contrast medium contained in the syringe 4 are thus mixed uniformly and distributed within it.

After a time interval that can be preset, the electronic unit CU stops the first motor means 17 and starts the second actuation means 6 and the third actuation means 9 to purge the infusion line, the outlet of which is not yet connected to the tube for feeding to the patient.

Once purging of the infusion line has ended and once its outlet has been connected to the tube for feeding to a patient, the electronic unit CU automatically restarts the first motor means 17 for another period of time during which the microbubbles of the contrast medium contained in the syringe 4, which is oscillated about the axis A, are mixed and distributed uniformly inside it, the pusher 36 of the second actuation means 6 having been moved away beforehand from the plunger 4b.

The medical personnel assigned to performing the sonogram, at its own discretion and despite having both hands occupied in operating the sonogram probe and in managing the processing of the images that it transmits to a monitor, then activates, by action on the foot pedal, the operation of the pump 1 to infuse the contrast medium and then automatically infuse the physiological solution without further interventions of any health personnel.

Once this time interval has elapsed, the electronic unit starts the second motor means 34 of the second actuation means 6 in order to infuse the contrast medium, as shown by arrow G. The end of the infusion is reported by the sensors 41, which report to the electronic unit CU that the stroke limit has been reached by the corresponding slider 30.

Once the second motor means 34 of the second actuation means 6 have stopped, the electronic unit CU starts the second motor means 34 of the third actuation means 9 in order to infuse in succession the physiological solution, as shown by the arrow H. As before, the end of this second infusion is reported by the corresponding sensors 41, which report to the electronic unit CU that the stroke limit has been reached by the corresponding slider 30.

Finally, the electronic unit reverses the rotation of the second motor means 34 and of the second and third actuation means 6 and 9 in order to return the corresponding pushers 36 to the beginning positions of their stroke, as shown by arrows L.

It should be noted that the initial position of the two plungers 4b and 8b, which depends on the amounts of contrast medium and of physiological solution loaded in the corresponding syringes, is detected simultaneously by the pressure sensing means 14 and by the rotation sensors 42. The former report the contact pressure with the plungers 4b and 8b and the latter report the number of turns made by the respective second motor means 34 before reaching the plungers 4b and 8b.

The pressure sensing means 14 further allow the detection during infusion of any abnormal increase in pressure on the plungers 4b and 8b, which indicates for example a venous occlusion.

This technique can be used for diagnosis for example in cardiology, neurology, gastroenterology, or for targeted therapeutic treatments.

The operation of the pump 1 in possible different applications can be deduced easily by the person skilled in the art. It can be used whenever it is necessary to mix the components of a fluid to be infused.

In practice it has been found that the described invention achieves the intended aim and objects. The pump according to the invention in fact allows one to automate not only the draining and infusion but also the mixing of the fluid to be infused, to mix the fluid homogeneously, precisely and in a short time without the intervention of auxiliary health personnel, and this accordingly entails a reduction of labor costs and of wastes of material, and allows medical personnel to perform mixing and infusion automatically and autonomously.

Finally, it should be noted that the alternated rotation of the syringe that contains the fluid to be mixed about an axis that is substantially perpendicular to the longitudinal axis of the syringe causes shaking and entrainment of the fluid between the two ends of the syringe, and this ensures uniform mixing, which cannot otherwise be obtained if the rotation of the syringe occurs about the longitudinal axis thereof. Due to the low viscosity of the fluids that are normally used, they in fact would not be entrained in rotation and therefore would not be stirred correctly.

The invention thus conceived is susceptible of numerous modifications and variations, all of which are within the scope of the appended claims. All the details may further be replaced with other technically equivalent ones. In practice, the materials used, as well as the shapes and the dimensions, may be any according to requirements without thereby abandoning the scope of the protection of the appended claim.

The disclosures in Italian Patent Application No, M02004A000028 from which this application claims priority are incorporated herein by reference.

What is claimed is:

1. In combination with a syringe extending along a longitudinal axis and having a cylindrical body and an axially shiftable plunger, an infusion pump comprising:
   a base;
   a holder for holding the syringe and pivotal on the base about a first axis substantially perpendicular to the longitudinal axis of said syringe, the holder having a tubular element adapted to grip the cylindrical body of the syringe;
   a shaft extending along the first axis and supported for rotation about the first axis on the base;
   first motor means coupled to the shaft;
   a coupling securing the holder to the shaft and of a type selectable from interlocking and/or contrast and/or friction coupling means, the coupling comprising a seat for containing the holder, formed in the shaft, and provided with cavities in which corresponding protrusions formed in the holder are insertable, whereby the holder can oscillate about the first axis relative to the base;
   a pusher displaceable linearly on the base transversely of the first axis;
   second actuation means for pressing the pusher against the plunger and thereby sliding the plunger of said syringe;
   a controller connected to first actuation means and to the second actuating means for moving the pusher out of engagement with the plunger during oscillation of the syringe about the first axis and for operating the second actuation means only when the first actuation means is not oscillating the syringe to express contents of the syringe;
   an auxiliary syringe with a plunger thereof;
   locking means for locking the auxiliary syringe mounted on the base;
   third actuation means for sliding the plunger of the auxiliary syringe;
   a stem;
   elastic means; and
   a guide, the holder comprising a portion that has a contoured profile for mating with a head of the stem that is inserted so as to be axially slidable, with interposition of the elastic means, in the guide that is formed in the shaft at the seat, the head protruding into the seat, a coupling between the head and the contoured portion being suitable to fix the holder to the shaft.

2. The pump of claim 1 wherein said first axis lies on a substantially horizontal plane.

3. The pump according to claim 1 wherein said holder is adapted to perform alternating rotation about said first axis at an angle that is less than 2 πrad.

4. The pump of claim 1 wherein at least one of said first, second and third actuation means is automated.

5. The pump of claim 1, further comprising
   first sensing means for sensing presence of said syringe.

6. The pump of claim 5, further comprising
   second sensing means for sensing presence of said auxiliary syringe.

7. The pump of claim 6 wherein at least one of said first and second sensing means comprises a switch of the ON/OFF type.

8. The pump of claim 5 wherein said first sensing means are connected with said shaft.

9. The pump of claim 8 wherein an end of said stem that lies opposite said head protrudes externally from said shaft, said first sensing means being arranged proximate thereto, said stem being adapted to actuate said first sensing means.

10. The pump of claim 1, further comprising
    first control means for controlling the sliding of the plunger of said syringe.

11. The pump of claim 10, further comprising
    second control means for controlling the sliding of the plunger of said auxiliary syringe.

12. The pump of claim 1 wherein at least one of said first and second actuation means is associated with pressure sensing means for sensing pressure applied to the plunger of the respective syringe.

13. The pump of claim 12 wherein at least one of said second and third actuation means is effective linearly.

14. The pump of claim 12 wherein at least one of said first, second and third actuation means is mechanical.

15. The pump of claim 12 wherein at least one of said first, second and third actuation means is pneumatic or hydraulic.

16. The pump of claim 12 wherein at least one of said first, second and third actuation means is electrical.

17. The pump of claim 12 wherein at least one of said first, second and third actuation means is electromechanical.

18. The pump of claim 1, comprising ON/OFF control means for activating and deactivating operation of the second and third actuation means.

19. The pump of claim 18 wherein said ON/OFF control means have a pedal or a pushbutton and are foot actuatable.

20. The pump of claim 19 wherein said ON/OFF control means are adapted to convey an ON/OFF signal via a cable, wireless connection, or infrared signal.

21. The pump of claim 1 wherein the controller is an electronic control and monitoring unit.

22. The pump of claim 21 wherein said electronic control and monitoring unit is programmable.

23. The pump of claim 1 wherein said locking means comprise a receptacle for accommodating wings formed at an inlet end of said cylindrical body of the auxiliary syringe, and a clamp for locking said cylindrical body.

24. In combination with a syringe extending along a longitudinal axis and having an axially shiftable plunger, an infusion pump comprising:
   a base;
   a holder for holding the syringe and pivotal on the base about a first axis substantially perpendicular to the longitudinal axis of the syringe;
   first actuation means connected between the base and the holder for oscillating the holder about the first axis relative to the base;
   a first pusher displaceable linearly on the base transversely of the first axis;
   second actuation means for pressing the pusher against the plunger and thereby sliding the plunger of the syringe;
   a controller connected to first actuation means and to the second actuating means for moving the pusher out of engagement with the plunger during oscillation of the syringe about the first axis and for operating the second actuation means only when the first actuation means is not oscillating the syringe to express contents of the syringe;
   an auxiliary syringe with a plunger thereof;
   locking means for locking the auxiliary syringe mounted on the base;
   third actuation means for sliding the plunger of the auxiliary syringe, at least one of the second and third actuation means being associated with pressure sensing means for sensing pressure applied to the plunger of the respective syringe;

a slider, at least one of said second and third actuation means comprising straight guiding means along which said slider is associated for alternate sliding;

a screw substantially parallel to said straight guiding means, supported for rotation by said base, and coupled to a female thread formed in said slider;

motor means connected with said screw; and a second pusher rigidly associated with said slider and provided so as to make contact with the plunger of said syringe or of said auxiliary syringe.

25. The pump of claim 24 wherein said motor means is a stepping motor.

26. The pump of claim 25 wherein said motor means comprises an inverter.

27. The pump of claim 24 wherein said controller comprises position sensors selectable among proximity sensors, and switches able to sense a position of said slider, and sensors for detecting rotation of said screw.

28. The pump of claim 24 wherein said pressure sensing means comprise a load cell associated with said first pusher.

* * * * *